United States Patent [19]

Huprich et al.

[11] Patent Number: 5,688,498
[45] Date of Patent: Nov. 18, 1997

[54] METHOD AND COMPOSITION FOR COATING WOUND OR PROTECTING ANIMAL SKIN

[75] Inventors: Carl A. Huprich, Robertsdale, Ala.; Leo L. Timms, Ames, Iowa

[73] Assignee: Iowa State University Research Foundation, Inc., Ames, Iowa

[21] Appl. No.: 644,009

[22] Filed: May 9, 1996

[51] Int. Cl.$^6$ .............................. A61K 9/10; A61L 25/00
[52] U.S. Cl. ........................... 424/78.02; 424/78.06
[58] Field of Search .................... 424/78.03, 78.02, 424/78.06

[56] References Cited

U.S. PATENT DOCUMENTS 5,192,536  3/1993  Huprich ........................ 424/78.08
5,413,780  5/1995  Huprich ........................ 424/78.05

OTHER PUBLICATIONS

Hackh's Chemical Dictionary Fourth Ed. 1969 p.89.

Primary Examiner—Peter F. Kulkosky
Attorney, Agent, or Firm—Zarley,McKee,Thomte,Voorhees, & Sease

[57] ABSTRACT

Solutions of polyether polyurethane with benzoin gum in tetrahydrafuran applied to animal skin provide dry films that are elastic, vapor permeable, water proof, dirt proof, insect proof, aerobic bacteriostatic and adhere well under environmental conditions. Apparent application viscosity can be adjusted as required for specific needs.

6 Claims, No Drawings

METHOD AND COMPOSITION FOR COATING WOUND OR PROTECTING ANIMAL SKIN

BACKGROUND

Protecting wounds and animal skin from damage by environment, abrasion, wind, dirt, water, insect bites, etc. has been difficult. Most treatments are ineffective or require replacement frequently and may aggravate the conditions present. U.S. Pat. No. 5,192,536 discloses covering a successful method and composition for coating a wound with polyether polyurethane. This is useful and overcomes most of the problems inherent with conventional treatment. The issued patent listed related technology. This application covers improvements. Obviously adhesion time affects the protection provided. The application techniques are important to provide complete rather than partial protection; i.e., dip, spray, spread, wipe, etc. Formulation and composition affect these considerations.

SUMMARY

Polyether polyurethane dissolved in tetrahydrofuran provides a solution that can be applied to animal skin and dries rapidly to an elastic film that is vapor permeable, water proof, wind proof, dirt proof, insect proof, etc. This film protects the skin from further damage during the healing process or exposure. Adhesion to the skin is improved by the addition of benzoin. Application technology and techniques are affected by apparent viscosity. Apparent viscosity is affected by concentration of solids, type of solids, and solvents. These are adjusted to meet specific needs.

DESCRIPTION

U.S. Pat. No. 5,192,536 discloses a method and composition for coating a wound with polyether polyurethane. This application covers improvements to the formulation and technology developed since application and issuance of that patent.

Adhesion of the film produced affects the length and completeness of protection. Apparent viscosity of the solution affects the application efficacy and technology or techniques and resultant adequacy of protection. Prevention of attack by outside elements reduces adverse effects of the environment.

Specifically, addition of 5% benzoin gum to the solution almost doubled the adhesion time of the coated skin. Other percentages affected the useful service life also.

Specificallly: changing the solvent percentage converted the original formulation from a spreadable solution into a dippable solution suitable for body extensions like teats, and limbs.

One combination follows:

100 parts tetrahydrofuran 10 parts polyether polyurethane pellets 5 part benzoin gum.

We claim:

1. A solution of polyether polyurethane in tetrahydrofuran containing benzoin gum wherein said solution upon drying to an elastic film has improved adhesion as compared to the same solution without benzoin gum.

2. A solution according to claim 1 wherein the benzoin gum is present in an amount of 5%.

3. A solution according to claim 1 comprising:

100 parts of the tetrahydrofuran;

10 parts of the polyether polyurethane;

5 parts of the benzoin gum.

4. A process for applying the solution of claim 1, wherein the amount of benzoin is varied to allow for more effective coverage of the desired surface area as necessary.

5. A process for protecting animal skin comprising applying a solution of claim 1 comprising polyether polyurethane, tetrahydrofuran, and benzoin gum to the animal skin.

6. A process according to claim 5 wherein the solution is applied to the skin using a method selected from the group consisting of dipping, spraying, spreading, and wiping.

* * * * *